United States Patent
Nomura et al.

(10) Patent No.: US 6,967,105 B2
(45) Date of Patent: Nov. 22, 2005

(54) SURFACE-MODIFIED WICK FOR DIAGNOSTIC TEST STRIP

(75) Inventors: Hiroshi Nomura, Shorewood, MN (US); Arthur R. Kydd, St. Paul, MN (US); August R. Hanson, Rosemount, MN (US); Robert J. Petersen, Minneapolis, MN (US)

(73) Assignee: QuestStar Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/728,153

(22) Filed: Dec. 2, 2000

(65) Prior Publication Data

US 2002/0102739 A1 Aug. 1, 2002

(51) Int. Cl.$^7$ .............................................. G01N 21/77
(52) U.S. Cl. ........................ 436/169; 436/164; 422/55; 422/56; 422/58; 422/68.1; 422/82.05
(58) Field of Search .............................. 422/55, 56, 58, 422/68.1, 73, 82.05; 436/69, 164, 177, 169

(56) References Cited

U.S. PATENT DOCUMENTS

| | | | |
|---|---|---|---|
| 4,806,246 A | | 2/1989 | Nomura |
| 5,246,666 A | * | 9/1993 | Vogler et al. .................. 422/73 |
| 5,296,192 A | | 3/1994 | Carroll |
| 5,344,462 A | * | 9/1994 | Paskalov et al. ........... 8/115.52 |
| 5,536,413 A | * | 7/1996 | Bormann et al. ............ 210/650 |
| 5,843,789 A | * | 12/1998 | Nomura et al. .............. 436/164 |
| 6,040,195 A | | 3/2000 | Carroll |
| 6,203,850 B1 | | 3/2001 | Nomura |
| 6,284,550 B1 | | 9/2001 | Carroll |

FOREIGN PATENT DOCUMENTS

WO      WO 00/69548      * 12/2000

OTHER PUBLICATIONS

H. Yasuda, "Plasma Polymerization", Academic Press, 1985, pp 345–354.

* cited by examiner

*Primary Examiner*—Jill Warden
*Assistant Examiner*—LaToya Cross
(74) *Attorney, Agent, or Firm*—Altera Law Group, LLC

(57) ABSTRACT

A wicking material is disclosed that exhibits a horizontal wicking velocity of at least about 1.0 millimeter per second when contacted with a physiological fluid such as blood, lymph or cellular interstitial fluid. This high wicking rate is achieved by means of treatment of a fibrous wicking material candidate with a low temperature gas plasma, particularly a glow discharge gas plasma formed in a gaseous blend made up predominantly of a mixture of oxygen with a saturated alkane chosen from the group consisting of methane, ethane and propane. Diagnostic test strips made with the surface-modified wicking material, and containing an immobilized reagent means for analysis of an analyte in a physiological fluid, show improved performance in terms of increased accuracy, finer precision of analyses, reduced time of analysis, a smaller fluid sample size requirement, and improved compliance with manufacturing standards resulting in lower manufacturing costs blood sugar determinations.

20 Claims, 4 Drawing Sheets

SURFACE-MODIFIED WICK FOR DIAGNOSTIC TEST STRIP

FIELD OF THE INVENTION

The present invention relates to a diagnostic test strip for chemical analysis, and more particularly to an improved wick and diagnostic test strip containing the wick for analysis of chemicals such as blood sugar in diabetics.

BACKGROUND OF THE INVENTION

Many medical etiologies can be monitored periodically by analysis of a sample of a body fluid for the presence and level of a specific solute or component in the fluid. The most widely known example is the measurement of glucose levels in blood or interstitial fluid, pertaining to monitoring, treatment and control of diabetes mellitus.

Prior art blood glucose measurement devices have operated on the principle of taking blood from an individual by a variety of methods, such as by needle or lance, followed by contacting a diagnostic strip with a portion of the blood sample. Some recent devices appear to extract a sample of interstitial fluid rather than blood for purposes of the same type of analyses. The diagnostic test strip typically consists of a paper or microporous polymeric film which has been impregnated with a set of chemicals that, upon contact with the fluid, produce a measurable chemical reaction consistent with both the presence and concentration of a targeted analyte in the fluid. Most such test strips produce a color change, the spectral band and intensity of which are measured photometrically and correlated with analyte concentration. Numerous blood glucose meters are on the market which measure the level of blood glucose by color changes on test strips. Competition between manufacturers of these devices includes, in addition to cost, claims for accuracy, precision, small sample size, and, very importantly, speed of analysis. The latter-most factor becomes very important to a patient when all the other factors are balanced out.

One of the prior art devices presently in commercial use is a monitor/combination incorporating features disclosed and described in U.S. Pat. No. 4,787,398, wherein a hand-held, pocketable, diagnostic monitoring system contains a lancet unit and a means for accepting and reading a disposable diagnostic test strip upon which a droplet of blood is deposited. The disposable test strip contains a reagent package including glucose oxidase and a color-producing substrate, and a wicking means to distribute fluid from a blood droplet to the reagent package, which itself is immobilized on a porous medium addressable by a light source and a light sensing means. The wicking means is commonly a woven cotton-containing fabric, chosen because of the wettability and wicking nature of cotton fibers. Such fabrics are typically a blend of cotton and polyester. Such fabrics achieve a wicking delivery of a fluid such as blood to the reagent package, but not without drawbacks. One key factor is the relatively slow speed of wicking associated with this fabric. Another key factor is the characteristic of the cotton to absorb a portion of the fluid, such that the amount available to be delivered to the reagent package is significantly diminished. As a result, a greater amount a fluid, such as the blood droplet size, is required for analysis, and inadequate sample size or delivery often results in no reading or improper reading in a blood glucose monitor.

One significant aspect and feature of the present invention is a diagnostic test strip with an improved wicking material that provides a far greater rate of fluid transfer than presently available, so as to reduce the time necessary for sample fluid delivery to an immobilized reagent package, and thereby improve the speed of analysis.

Another significant aspect and feature of the present invention is a diagnostic test strip with an improved wicking material that provides a more even delivery of sample fluid to an immobilized reagent package, so as thereby to improve the precision and accuracy of analysis.

A further significant aspect and feature of the present invention is a diagnostic test strip that delivers a sample fluid to immobilized reagent package with such reliability, that a greater overall number of test strips meet manufacturing standards, resulting in little or no rejects and thereby lower overall manufacturing costs, ultimately resulting in lower overall cost to the patient.

These and other objects and attendant advantages of the present invention will be readily appreciated and understood by reference to the following summary of the invention and detailed description, considered in connection with the accompanying drawings.

SUMMARY OF THE INVENTION

The present invention embodies a wicking material in the form of a sheet or cloth that exhibits a horizontal wicking velocity of at least about 1.0 millimeter per second when contacted with an aqueous fluid, particularly a physiological fluid such as blood, lymph or cellular interstitial fluid. The invention further embodies the above wicking material, wherein the horizontal wicking velocity of at least about 1.0 millimeter per second is achieved by means of treatment of a fibrous wicking material candidate with a low temperature gas plasma. In a preferred embodiment, the wicking material consists of a fabric that has been modified by treatment with a glow discharge gas plasma formed in a gaseous blend made up predominantly of a mixture of oxygen with a saturated alkane chosen from the group consisting of methane, ethane and propane.

The present invention also embodies a diagnostic test strip that provides an immobilized reagent means targeted toward an analyte in a fluid, a planar wicking material in contact with the immobilized reagent means that provides a site for acceptance of a sample of a fluid such as a droplet of blood and which distributes a portion of that sample to the immobilized reagent means by a wicking process, and a holder for carrying the reagent means and the wicking material, wherein the planar wicking material exhibits a horizontal fluid wicking velocity of at least about 1.0 millimeter per second in the plane of the material. The present invention also embodies in a preferred embodiment a diagnostic test strip that provides, in addition to the aforementioned immobilized reagent means, planar wicking material and holder for carrying the reagent means and the wicking material, an indicator means for detection of wicking movement of fluid beyond the area of contact with the immobilized reagent means whereby adequate contact with the reagent means is assured, wherein again the planar wicking material exhibits a horizontal fluid wicking velocity of at least about 1.0 millimeter per second in the plane of the material. In conjunction with a device employing a system for reading the diagnostic test strip, the indicator means for detection of wicking movement of fluid provides a timing point or endpoint for basing the measurement of the development of a response in the immobilized reagent means to an analyte such as blood glucose and its correlation to concentration of the fluid analyte.

Diagnostic test strips made in accordance with the present invention show various advantages, including advantages in terms of increased accuracy, finer precision of analyses, reduced time of analysis, a smaller fluid sample size requirement, and improved compliance with manufacturing standards resulting in lower manufacturing costs.

LIST OF FIGURES

DETAILED DESCRIPTION OF THE INVENTION

In accordance with the present invention, a diagnostic test strip is herein disclosed which incorporates an immobilized reagent means that is selectively responsive to one or more solutes or components (such as glucose) in a fluid (such as blood, lymph or interstitial fluid), a wicking material which has a portion of same in contact with the immobilized reagent means and which delivers a fluid to the immobilized reagent means by a wicking process from a site of application of a sample of a fluid thereto, the diagnostic test strip also including a holder for carrying the reagent means and the wicking material. A diagnostic test strip of this general configuration is described in the aforementioned U.S. Pat. No. 4,787,398 which is herein incorporated by reference.

Figure 1:
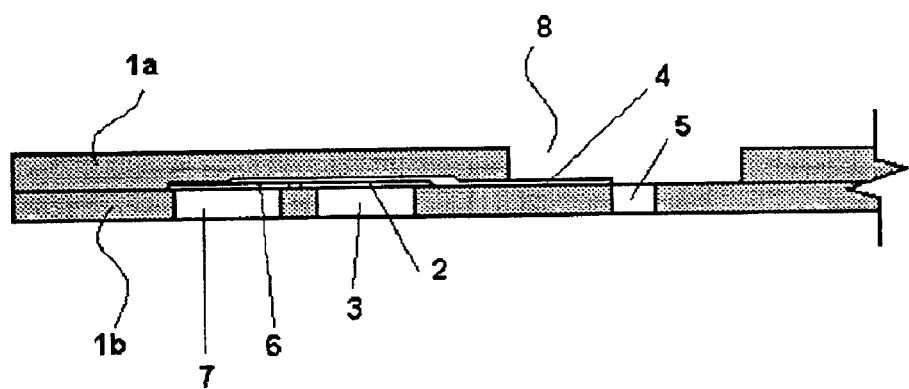
FIG. 1 illustrates a cross sectional view of a diagnostic test strip.
Figure 2:
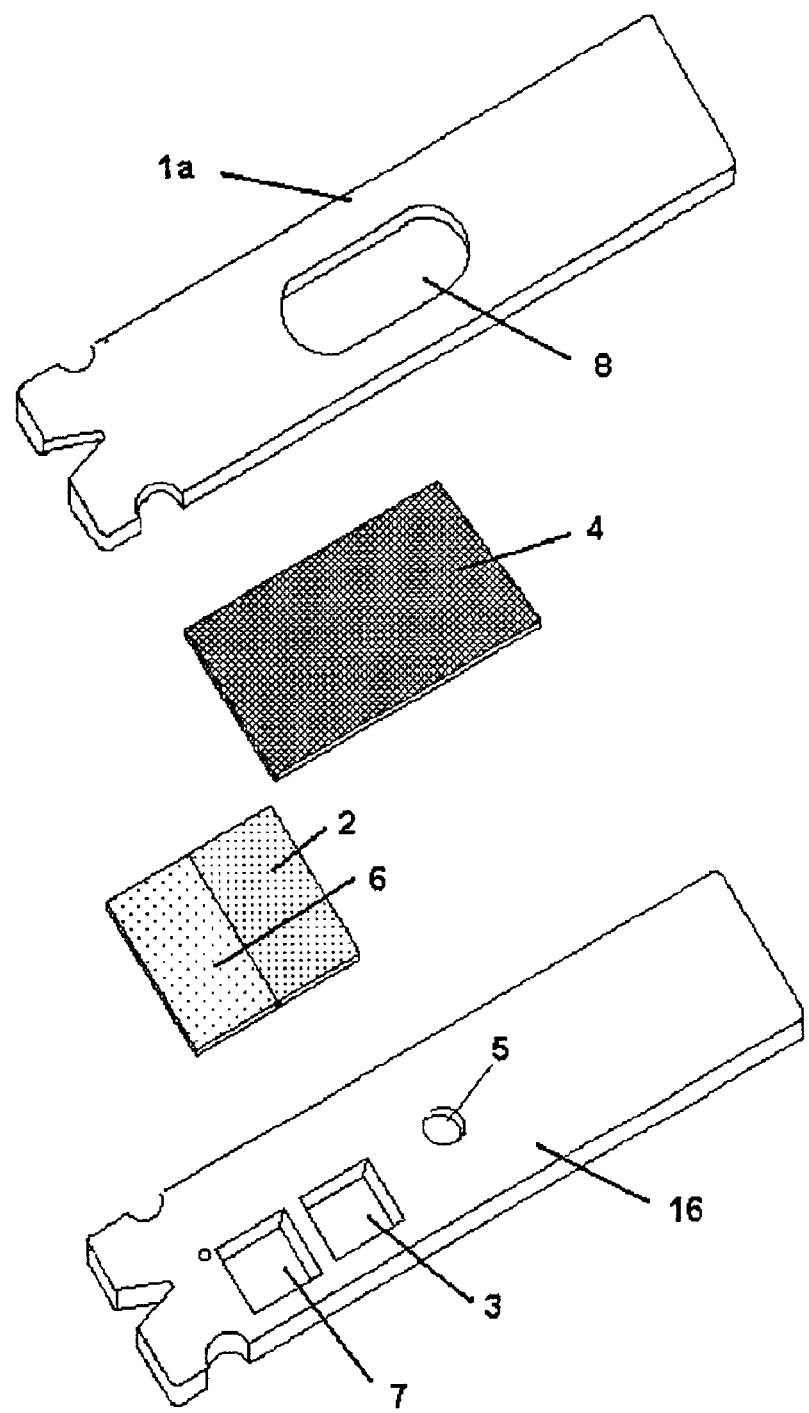
FIG. 2 illustrates an exploded view of a diagnostic test strip corresponding to FIG. 1.

FIG. 1 illustrates an example of a preferred embodiment of a diagnostic test strip useful within the context of the present invention. With reference to FIG. 1, a holder consisting of top and bottom layers 1a and 1b provides a mounting for an immobilized reagent means 2 in a manner so as to anchor a portion of the immobilized reagent means within a window provided by a first aperture 3 in the bottom layer 1b. The holder also provides a mounting for a wicking material 4 made in accordance with the present invention, locating the wicking material in a position so as to provide both a site for application of a fluid sample (such as a droplet of blood) and a site for wicking delivery of a portion of the fluid sample to the immobilized reagent means 2. The holder may also provide, as shown in FIG. 1, an aperture 5 for travel of a lancet there-through as part of a procedure for blood collection by a finger pricking method. The holder may further provide a mounting for a lot calibration paper 6 anchored within a window provided by a third aperture 7, wherein the lot calibration paper 6 is in at least partial contact with the wicking material 4, and can serve as a means of detection of fluid movement within the wicking material. A wide aperture 8 in the top layer 1a of the holder provides a sample bowl for both transit of a lancet being projected through the underlying aperture 5 and for application of a sample droplet of blood or other fluid onto the wicking material. The arrangement of layers in FIG. 1 is shown as an exploded view in FIG. 2, wherein the lot calibration paper 6 and a reagent means 2 are juxtaposed and drape over a lot calibration window aperture 7 and a reagent means window aperture 3 respectively, wherein also the wicking material layer 4 extends completely over the immobilized reagent means layer 2 and onto at least a portion of the lot calibration paper 6.

In a typical use of a diagnostic test strip of this design, a patient will prick a finger by means of a lancet, then place a droplet of expressed blood onto the wicking material from the top side at a site within the sample bowl A portion of the blood droplet is wicked into the direction of the lot calibration paper, contacting the immobilized reagent means in the meanwhile, whereupon a discernible and measurable chemical reaction begins. Quickly thereafter, the lot calibration paper changes appearance due to wetting by wicked fluid. A detection system, employing for instance a light emitting diode LED light source and photoelectric detector, detects, times, and measures a color change reaction, which is then correlated with blood glucose concentration.

The immobilized reagent means will generally consist of a microporous polymeric material that has been impregnated with a combination of chemicals. These chemicals are advantageously chosen to produce a measurable chemical reaction upon contact with a targeted analyte, when the analyte is present in a sample fluid and the fluid is brought into contact with the microporous polymeric material by the wicking material. In the case of blood glucose determinations, the microporous polymeric material is most often a microporous polyamide (nylon), which has been impregnated with a glucose oxidase enzyme and a color-producing chemical. Many such combinations have been disclosed in patents and scientific publications, and several are in commercial use. Pertaining to microporous polyamide membranes, examples of such are disclosed and described in U.S. Pat. Nos. 4,340,479 and 4,340,480.

The lot calibration paper can be essentially any paper that exhibits a discernible change in appearance upon being wetted with a sample fluid. By discernible change is meant, for example, a change in appearance which alters the frequency and/or intensity of reflected light, which is incident upon the paper surface from a light source and reflected therefrom to a light detector. Such a paper is preferably a cellulosic paper of a grade similar to a common xerographic-grade paper, but which may be tinted to a preselected shade of gray relating to a calibration of the juxtaposed reagent means and the latter's lot-based range of color change, as disclosed in the aforementioned U.S. Pat. No. 4,787,398.

Figure 3:
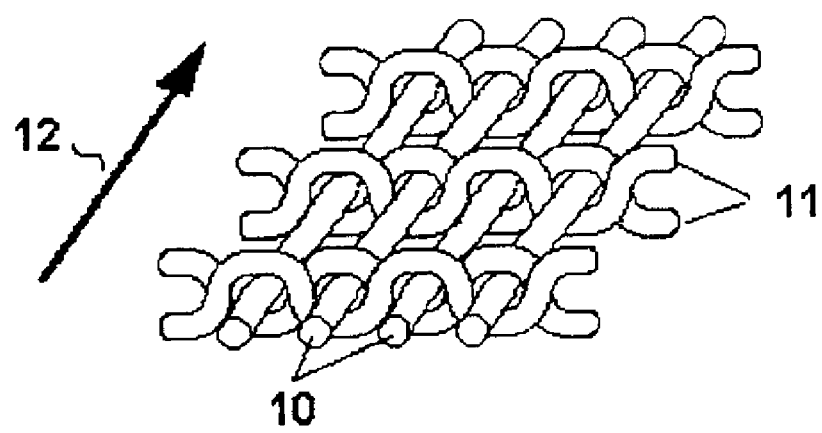
FIG. 3 illustrates a wicking fabric weave with preferred wicking direction indicated.

Turning now to the wicking material, a wicking material that exhibits a horizontal fluid wicking velocity of at least about 1.0 millimeter per second in accord with the present invention is preferably composed of a sheet or fabric that will allow wicking flow of a fluid, and which achieves this wicking rate as a result of having its surfaces modified by exposure to a low temperature gas plasma. The sheet or fabric may be a nonwoven material, made by either a wet-laid or dry-laid process. Alternatively, the wicking material may consist of a woven or knitted fabric. Further in this regard, a simple weave fabric oriented in the direction of wicking movement is preferred. This is illustrated by means of FIG. 3, wherein the woof fibers 10 are oriented in the intended direction of wicking (shown by the arrow 12), and the warp fibers 11 are transverse to the direction of wicking 12. This arrangement provides for augmented wicking along generally straight channels associated with the generally straight alignment of the woof fibers. In this regard, prior art woven fabrics have consisted of woven cotton or of a cotton-containing blended fiber composition (such as cotton-polyester fabrics), because of the natural wicking nature of the cotton. An example of such a wicking material is a 50:50 cotton/polyester blend made by Spring Industries, Inc., Rock Hill, S.C., under the designation Bounce Lint Free. However, in the preferred embodiment of the present invention, the presence of cotton in the fabric is not required, and in fact the surface modification used in the present invention serves to correct one of the drawbacks of cotton, which is its absorption of blood fluid. An example of an alternative fabric wicking material would be a knitted polyester tricot such as used as a water permeate channel spacer in reverse osmosis spiral elements, and which is modified by the surface treatment disclosed in the present invention.

The wicking material is surface-modified by exposure to a low temperature gas plasma, preferably a gas plasma containing excited species derived from gaseous oxygen in combination with a low molecular weight gaseous alkane such as methane, ethane, or propane. Particularly preferable is a wicking material treated by exposure to a gas plasma formed in a gaseous blend of methane and oxygen. The treatment of the wicking material preferably entails conditions wherein all surfaces of the wicking material are exposed and modified by the gas plasma, including top surface, bottom surface, and interstitial areal surfaces within the material. By means of this treatment, wicking materials with a horizontal wicking rate of at least about 1.0 millimeter per second, more preferably at least about 1.5 millimeters per second, most preferably at least about 2.0 millimeters per second, are obtained in accord with the present invention. Untreated wicking material candidates show approximately one-fourth to one-twentieth of these wicking rates, measured under essentially identical conditions. Thus, the wicking materials of the present invention exhibit at least about a four-fold (400%) increase in wicking rate towards a sample fluid and particularly a physiological fluid such as blood, lymph or interstitial fluid, and can exhibit even about a thirty-fold (3,000%) increase in wicking rate in some embodiments compared with nontreated wicking material candidates.

Treated wicking materials are prepared from wicking material candidates by exposure to a glow discharge gas plasma and a concomitant modification of the material's surfaces thereby. The glow discharge gas plasma, also commonly referred to as a low temperature gas plasma, is preferably generated in a vacuum chamber by means of a glow discharge initiated and maintained through a gas or blend of gases. The glow discharge may be initiated by means of an audio frequency, a microwave frequency or a radiofrequency field transmitted to or through a zone in the vacuum chamber. Particularly preferred is the use of a radiofrequency (RF) discharge, transmitted through a spatial zone in the vacuum chamber by an electrode connected to an RF signal generator. A more localized and intensified gas plasma is attained by means of an electrode pair, whereas a more diffuse gas plasma is a result of a single electrode. A rather broad range of RF signal frequencies starting as low as 50 kHz may be used in causing and maintaining a glow discharge through the monomer vapor. In commercial scale usage of RF plasma treatments, an assigned radiofrequency of 13.56 MHZ may be more preferable to use to avoid potential radio interference problems. Chambers may be of several overall designs, various examples of which are shown in U.S. Pat. Nos. 4,410,338, 5,439,736, 5,472,509, and 5,843,789, all of which are herein incorporated by reference. A general design particularly useful in producing on a continuous basis one or more lots of commercially significant lengths of treated wicking material is disclosed in U.S. Pat. Nos. 5,439,736 and 5,472,509, which are herein incorporated by reference. In this general design, a glow discharge reaction zone is advantageously situated between two large chambers, and material is fed from one chamber to the other, passing through the reaction zone. The speed of passage of the material through the glow discharge zone may be conveniently controlled so as to achieve a desired time of exposure of the wicking material to the gas plasma. The disposition of the wicking material within the glow discharge zone is preferably such as to achieve a generally uniform exposure of all sides of the material to the surface modifying characteristics of the gas plasma. Thus, for instance, the wicking material will preferably be drawn through the center of an established gaseous glow zone.

In the generation of a glow discharge gas plasma, the plasma gas pressure in the vacuum chamber may vary in the range of from 0.01 torr to 2.0 torr. Gas pressures are preferably in the range of 0.05 to 1.0 torr for best results. In the case of gas plasma treatment of fabrics by a methane/oxygen plasma, gas plasma pressures in the range of 0.2 to 0.6 torr (200 to 600 mtorr) have been found to be particularly optimal in surface modifications of cotton-polyester fabrics. To maintain desired pressure levels, and particularly to achieve steady state conditions, continuous inflow of gases to the plasma zone is normally practiced, along with continuous drawing off of the gases through a vacuum pumping apparatus. This approach also overcomes any change in gas compositions due to possible minor leakage of air through seals or joints. The glow discharge need not be continuous, but may be intermittent in nature during plasma treatment, but a continuous glow discharge is more preferably employed, especially when it is desirable to treat a continuous strand or roll of wicking material candidate. All of these chamber designs and operational considerations are well within the capabilities of one skilled in the art of low temperature gas plasma treatment of articles.

During the plasma treatment, some fragmentation of gases in the plasma zone occurs. For instance, molecular oxygen may be excited to an atomic oxygen state, and may be further excited to a radical ion state. Similarly, a normally nonpolymerizable gas such as methane may be fragmented to a methyl radical or radical ion, which can attach to a wicking material fiber surface, or which can combine with an oxygen atom to form another reactive radical or radical ion. These and other reactive radical fragments and intermediates are capable of modifying essentially all surfaces in contact with the gas plasma. The combination of oxygen and a low molecular weight alkane such as methane is desirable in the modification of the wicking material candidates, in that a this combination produces a very thin and very tightly crosslinked veneer on polymeric surfaces, wherein the veneer contains exposed hydrophilic groups that remain permanently fixed at the surface, whether it interfaces with air or with a liquid. The tightly crosslinked nature of the veneer is believed to be an invaluable attribute for maximum wicking performance, arising from extreme limitations on segmental motion in the veneer's polymeric matrix. Other means of generating hydrophilic surfaces, such as graft polymerization or solvent-deposited coatings, gives coating compositions with appreciable segmental motion, allowing surface-borne hydrophilic groups to be folded into the matrix away from interfacial contact.

Figure 4:
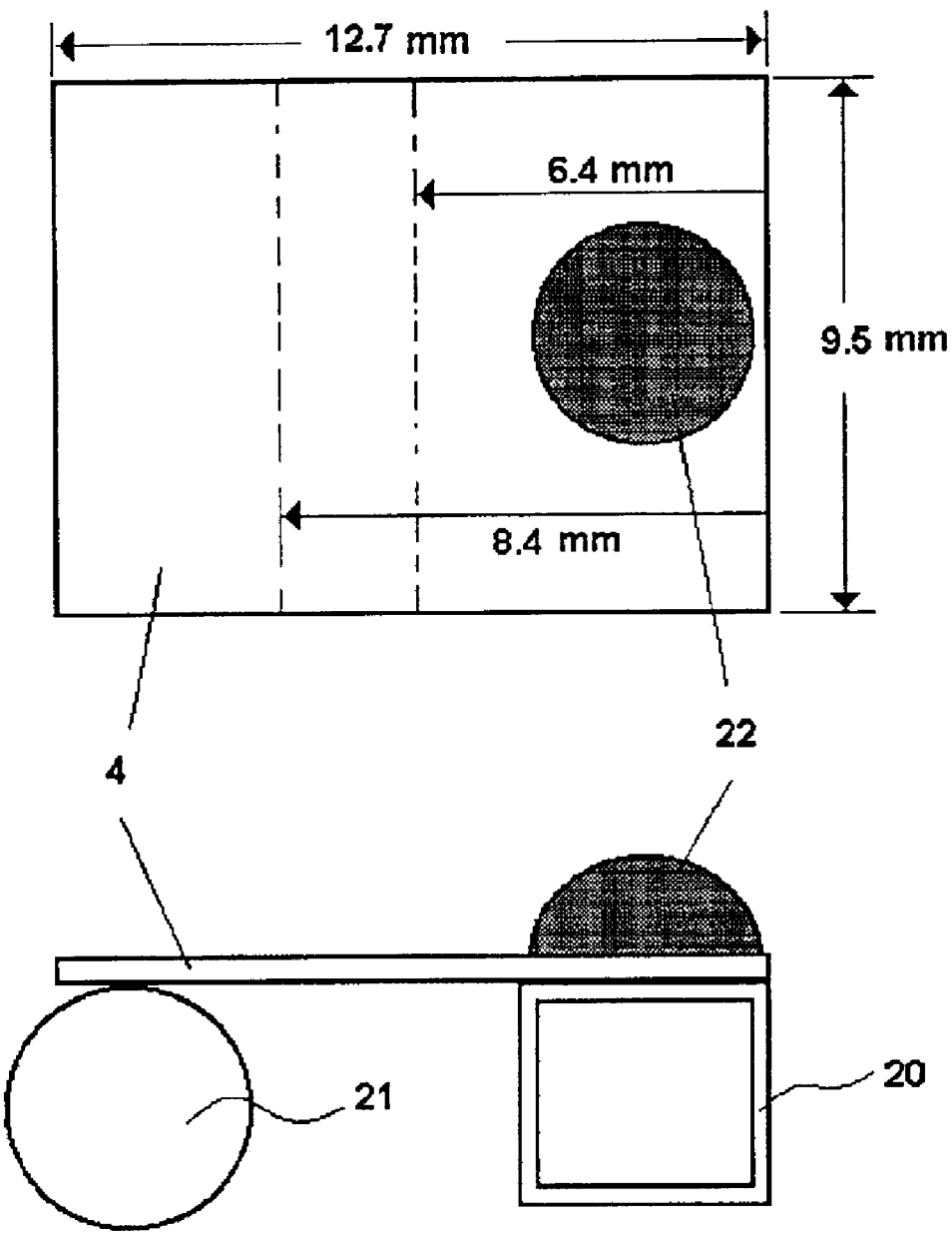
FIG. 4 illustrates a wicking velocity test configuration.

Turning now to examples demonstrating the effectiveness of the gas plasma-treated wicking materials in wicking fluid at high wick rates, a wicking test configuration as illustrated in FIG. 4 was employed to measure fluid wicking rates. This configuration consisted of a brass support 20, a glass rod support 21, and a sample of wicking material 4 supported horizontally over the two supports, with a gap of about 10 millimeters (mm) between the two supports as shown. Wicking material swatches of approximately 9.5 mm width and 12.7 mm length were used, also as indicated in FIG. 4. A droplet of whole blood (human), amounting to either 10 microliters or 20 microliters, was placed on the swatch at a point above the brass support. Then the liquid front was timed as it wicked horizontally toward the far end positioned over the glass rod. The rate of wicking of the blood fluid was timed over an distance interval of 2 mm, being the distance between the two dashed lines shown in FIG. 4. This arrangement provides a measure of horizontal wicking rates, and is chosen in part because any effects of gravity that might intervene in a non-horizontal test are minimized. It should be kept in mind, however, that wicking of a sample fluid will typically occur in all directions in the treated fabric. And, in fact, wicking in all directions, including vertically through the depth of the wicking material, is quite desirable. For instance, in the normal usage of the wicking material in the above-described diagnostic test strip, the sample of fluid must not only be transferred laterally but also vertically, so as to be delivered to the reagent means, the latter being located on the opposite face of the wicking material relative to the face upon which the droplet of fluid is deposited.

Turning now to actual examples of the surface modification of wicking materials and their resulting improvements in wicking rates and performance characteristics in diagnostic test strips, a gas plasma apparatus of the general design disclosed in U.S. Pat. Nos. 5,439,736 and 5,472,509 was used. Gas-plasma-treated wicking materials were prepared, unless otherwise indicated, by exposure for 5.75 seconds to an RF glow discharge plasma through a 3:2 ratio of oxygen to methane in a vacuum chamber at 400 mtorr pressure and 100 watts discharge power, wherein the oxygen/methane ratio was maintained by addition of 15.0 sccm (standard cubic centimeters per second) of oxygen and 10.0 sccm of methane to the gas plasma apparatus. Wicking material candidates chosen for the examples are shown in Table 1.These candidates from Spring Industries, Inc., all previously mentioned above, included two lots of Potentia Ivory (A and B), one of which was also first treated with an ionic surfactant (A2).

TABLE 1

| Fabric | Blend Ratio (polyester/cotton) | Thickness (mm) | Weave Pattern (warp/filling) | Ionic Surfactant |
|---|---|---|---|---|
| Bounce Lint Free | 50/50 | 0.23 | 104/48 | — |
| Potentia Exsol | 65/35 | 0.15 | 120/72 | — |
| Potentia Ivory A | 65/35 | 0.19 | 136/64 | no |
| Potentia Ivory A2 | 65/35 | 0.19 | 136/64 | yes |
| Potentia Ivory B | 65/35 | 0.19 | 136/64 | no |

EXAMPLES 1–5

The five fabrics listed in Table 1 were treated with an oxygen-methane glow discharge gas plasma as indicated above, and then were evaluated for wicking rate to whole blood using the arrangement shown in FIG. 4, with results shown in Table 2. A 20-microliter blood droplet size was used in the tests. Untreated wicking material candidates were used for controls to provide a basis of comparison, and are each listed as "Control" in the data in Table 2.

TABLE 2

| Fabric | Example Number | Wick Time sec./2 mm | Wick Rate mm/sec | Ratio to Control |
|---|---|---|---|---|
| Bounce Lint Free | Control | 9.1 | 0.22 | n/a |
| Bounce Lint Free | Example 1 | 1.6 | 1.25 | 5.9 |
| Potentia Exsol | Control | 4.7 | 0.43 | n/a |
| Potentia Exsol | Example 2 | 1.2 | 1.7 | 4.0 |

TABLE 2-continued

| Fabric | Example Number | Wick Time sec./2 mm | Wick Rate mm/sec | Ratio to Control |
|---|---|---|---|---|
| Potentia Ivory (A) | Control | 56.6 | 0.04 | n/a |
| Potentia Ivory (A) | Example 3 | 1.4 | 1.4 | 35.0 |
| Potentia Ivory (A2) | Control | 5.8 | 0.35 | n/a |
| Potentia Ivory (A2) | Example 4 | 1.3 | 1.6 | 4.5 |
| Potentia Ivory (B) | Control | 11.0 | 0.18 | n/a |
| Potentia Ivory (B) | Example 5 | 0.93 | 2.2 | 11.8 |

The data in Table 2 demonstrate that the examples exhibit wick rates of 1.3 to 2.2 mm/second, whereas the untreated controls show wick rates of only 0.04 to 0.35. The treated fabrics showed at least a four-fold greater wicking rate, that is, at least a 400% improvement. For the wicking candidate Potentia Ivory (sample A), the very slow initial wicking rate of the untreated control, which would be characteristic of a generally hydrophobic wick, was converted by glow discharge gas plasma treatment to a rapid wicking material with a wicking rate nearly equivalent to the other plasma-treated fabrics in these examples.

EXAMPLE 6

Bounce Lint Free was modified by oxygen/methane gas plasma treatment. Twelve reels of fabric 320 feet in length and 0.5 inch in width were modified. A sample from each reel was evaluated for wicking time with a blood droplet of 20 microliters, conducted as before. A sample of untreated fabric from the same lot was evaluated as a control. Table 3 lists the results of these evaluations. The reels of treated fabric exhibited an average blood wicking rate of 1.69 mm/sec, with a standard deviation of 0.20 mm/sec, whereas the untreated control exhibited a blood wicking rate of only 0.14 mm/sec, or about one-twelfth the rate of the treated reels.

TABLE 3

| Treated Fabric Reel Number | Wick Time sec./2 mm | Wick Rate mm/sec |
|---|---|---|
| Control | 14.5 | 0.14 |
| 1 | 0.99 | 2.02 |
| 2 | 1.08 | 1.85 |
| 3 | 1.07 | 1.87 |
| 4 | 1.16 | 1.72 |
| 5 | 0.99 | 2.02 |
| 6 | 1.08 | 1.85 |
| 7 | 0.91 | 2.20 |
| 8 | 1.00 | 2.00 |
| 9 | 1.18 | 1.69 |
| 10 | 1.31 | 1.53 |
| 11 | 1.28 | 1.57 |
| 12 | 1.18 | 1.69 |
| Average | 1.10 | 1.69 |
| Standard Deviation | 0.12 | 0.20 |

EXAMPLES 7–10

Bounce Lint Free fabric was modified by methane/oxygen plasma treatment at plasma conditions of 5.75 seconds exposure time to an RF glow discharge plasma through a blend of oxygen and methane in a vacuum chamber at 400 mtorr pressure and 100 watts discharge power, wherein the oxygen/methane blend was maintained by addition of 17.4 sccm of oxygen and 11.6 sccm of methane to the gas plasma apparatus. Four lots of 12 reels of wicking fabric candidate were processed to assess the reproducibility of the treatment process and range of consequent wick rates. Swatches from these reels were tested for wicking rates by the same procedure used in examples 1–6. Results are shown in Table 4. The data in Table 4 show average wicking rates for the treated candidates in the range from 2.29 to 2.59 mm/sec, which are about 27 to 31 times greater than the untreated candidate.

EXAMPLES 11

Bounce Lint Free fabric was surface-modified by a methane/oxygen plasma as in example 1. Diagnostic strips were fabricated with the surface-modified wicking material, and compared with essentially identical strips made with untreated Bounce Lint Free fabric. Two levels of glucose in whole blood, 50 and 100 milligrams per deciliter (mg/dl) were assayed, using droplet sizes of 10 microliters. Readings were taken using a CheckMate Plus® blood glucose monitoring system manufactured by QuestStar Medical, Inc. Three CheckMate Plus® meters were used, and nine test were run using each meter, for a total number of 54 test strip readings. Resulting data are gathered in Table 5. The data illustrated that the unmodified wick failed to provide valid endpoint analyses with this system—indicated by the notification "NEB" for "not-enough-blood"—for 96 percent of the tests, even though this system commonly assayed strips accurately at a 20-microliter blood droplet sample size. In contrast, the surface-modified wicking material gave

TABLE 4

| Control Reel Number | 0.083 mm/sec Ex. 7, mm/sec (Lot 145) | 0.083 mm/sec Ex. 8, mm/sec (Lot 146) | 0.083 mm/sec Ex. 9, mm/sec (Lot 147) | 0.083 mm/sec Ex. 10, mm/sec (Lot 148) |
|---|---|---|---|---|
| 1 | 2.53 | 2.63 | 2.25 | 2.78 |
| 2 | 2.30 | 2.60 | 2.63 | 2.44 |
| 3 | 2.22 | 2.60 | 3.08 | 3.45 |
| 4 | 2.08 | 1.85 | 2.00 | 2.00 |
| 5 | 2.86 | 2.53 | 2.17 | 2.82 |
| 6 | 2.38 | 2.63 | 2.00 | 2.00 |
| 7 | 2.15 | 2.56 | 3.08 | 2.94 |
| 8 | 1.98 | 2.74 | 2.00 | 2.00 |
| 9 | 2.22 | 2.35 | 2.63 | 2.50 |
| 10 | 2.44 | 3.23 | 3.39 | 3.39 |
| 11 | 2.06 | '—' | 2.44 | 2.63 |
| 12 | 2.27 | '—' | 2.53 | 2.15 |
| Average | 2.29 | 2.57 | 2.52 | 2.59 |
| Standard Deviation | 0.23 | 0.32 | 0.45 | 0.49 | valid readings in all but one instance under these same assay conditions. These data demonstrated that the surface modification of this cotton-containing wicking material resulted in less absorption of blood by the cotton, allowing for assay of a reduced blood sample size, while also utilizing a faster wick rate, as shown in the earlier examples.

TABLE 5

| | With Modified Wicking Material | | | With Unmodified Wicking Material | | |
|---|---|---|---|---|---|---|
| | Meter 1 | Meter 2 | Meter 3 | Meter 1 | Meter 2 | Meter 3 |
| Level 50 mg/dl Repetition | | | | | | |
| 1 | 60 | 53 | 57 | NEB | NEB | NEB |
| 2 | 58 | 60 | 47 | NEB | NEB | NEB |
| 3 | 54 | 57 | 53 | NEB | NEB | NEB |
| 4 | NEB | 55 | 47 | NEB | NEB | NEB |
| 5 | 55 | 55 | 56 | NEB | NEB | 49 |
| 6 | 59 | 60 | 53 | NEB | NEB | NEB |
| 7 | 54 | 48 | 53 | NEB | NEB | NEB |
| 8 | 58 | 54 | 58 | NEB | NEB | NEB |
| 9 | 57 | 53 | 53 | NEB | NEB | NEB |
| Mean | 56.9 | 55.0 | 53.0 | n/a | n/a | n/a |
| % NEB | | 3.7 | | | 96.3 | |
| Level 100 mg/dl | | | | | | |
| 1 | 106 | 95 | 92 | NEB | NEB | 49 |
| 2 | 107 | 102 | 112 | NEB | NEB | NEB |
| 3 | 89 | 94 | 119 | NEB | NEB | NEB |
| 4 | 96 | 100 | 104 | NEB | 117 | NEB |
| 5 | 104 | 92 | 98 | NEB | NEB | NEB |
| 6 | 102 | 98 | 119 | NEB | NEB | NEB |
| 7 | 106 | 96 | 111 | NEB | NEB | NEB |
| 8 | 94 | 94 | 94 | 93 | NEB | NEB |
| 9 | 109 | 95 | 98 | NEB | NEB | 96 |
| Mean | 101.4 | 96.2 | 105.2 | n/a | n/a | n/a |
| % NEB | | 0.0 | | | 85.2 | |

NEB = insufficient sample size; n/a = not applicable.

EXAMPLE 12

Bounce Lint Free fabric was surface-modified by a methane/oxygen plasma as in examples 7–10. Diagnostic test strips were fabricated with the surface-modified wicking material, and compared with test strips fabricated with Potentia Ivory (type A2). The latter test strips, using the surfactant-modified Potentia Ivory, perform sufficiently to be used generally as a market standard in these test strips. A blood glucose level of 350 mg/dl, which is an high level concentration encountered in diabetic patients at times and which represents a severe challenge for diagnostic test strips to accurately analyze, was used. Sample size was 20 microliters. Six meters were used for comparison readings, using nine strips of each type, for a total test series of 108 assays. Data are shown in Table 6. Test strips fabricated with the surface-modified wicking material exhibited a total mean value of 359.2 mg/dl, at a total coefficient of variance (% CV) of 6.0 percent. The test strips fabricated with the generally accepted Potentia Ivory wicking material exhibited a total mean value of 325.8 mg/dl, significantly understating the blood glucose concentration in this particular series of assays, and experienced a total coefficient of variance of 8.6 percent, wherein a % CV of 8.0 or less is generally sought as a standard.

Thus, the surface-modified wicking material provided improved performance in test strips designed to assay blood glucose, both in this example as to accurately measuring a very high glucose concentration, and in the earlier examples as to accurately measuring smaller blood sample sizes than possible with unmodified wicking materials. While these examples are provided to illustrate the nature and practice of the present invention and to illustrate the preferred mode of the present invention, the scope of the invention is not to be limited by the above examples, but is to be determined by the claims that follow.

TABLE 6

| | Modified Bounce Lint Free Meter Number | | | | | | Unmodified Potentia Ivory (Type A2) Meter Number | | | | | |
|---|---|---|---|---|---|---|---|---|---|---|---|---|
| | 1 | 2 | 3 | 4 | 5 | 6 | 1 | 2 | 3 | 4 | 5 | 6 |
| 1 | 353 | 341 | 365 | 395 | 385 | 373 | 318 | 336 | 290 | 314 | 326 | 330 |
| 2 | 316 | 356 | 327 | 354 | 347 | 348 | 305 | 355 | 350 | 339 | 324 | 321 |
| 3 | 387 | 359 | 362 | 358 | 357 | 380 | 419 | 339 | 305 | 333 | 351 | 317 |
| 4 | 394 | 336 | 334 | 343 | 317 | 356 | 344 | 315 | 348 | 328 | 350 | 390 |
| 5 | 347 | 406 | 349 | 374 | 377 | 376 | 343 | 327 | 360 | 343 | 301 | 293 |
| 6 | 385 | 348 | 361 | 395 | 347 | 358 | 338 | 299 | 332 | 355 | 337 | 332 |
| 7 | 391 | 344 | 308 | 390 | 338 | 393 | 335 | 337 | 296 | 301 | 334 | 290 |
| 8 | 361 | 357 | 380 | 373 | 345 | 352 | 270 | 337 | 332 | 329 | 283 | 310 |
| 9 | 365 | 358 | 338 | 327 | 344 | 368 | 292 | 302 | 277 | 317 | 316 | 300 |
| Mean | 367 | 356 | 347 | 368 | 351 | 367 | 329 | 327 | 321 | 332 | 325 | 320 |
| STDS | 25.7 | 20.5 | 22.4 | 24.0 | 20.3 | 14.8 | 42.1 | 18.6 | 29.8 | 15.8 | 22.2 | 30.2 |
| % CV | 7.0 | 5.7 | 6.4 | 6.5 | 5.8 | 4.0 | 12.8 | 5.7 | 9.3 | 4.8 | 6.8 | 9.4 |
| Total Mean | 359.2 | | | | | | 325.8 | | | | | |
| Total % CV | 6.0 | | | | | | 8.6 | | | | | |

We claim:

1. The method of analyzing an analyte in a physiological fluid comprising contacting with a wick with a sample of physiological fluid, and delivering a portion of the sample to an immobilized reagent means by wicking through the wick, wherein the wick comprises a fibrous wicking material in the form of a sheet or cloth that is surface-modified by exposure to a glow discharge gas plasma so as to exhibit a horizontal wicking rate of at least about 1.0 millimeter per second in contact with the physiological fluid.

2. The method according to claim 1 wherein the glow discharge gas plasma is formed in a gaseous blend composed predominantly of a mixture of oxygen with a saturated alkane chosen from the group consisting of methane, ethane and propane.

3. The method according to claim 2 wherein the fibrous wicking material consists of a woven cotton-polyester fabric.

4. The method according to claim 3 wherein the fibrous wicking material exhibits a horizontal wicking rate of at least about 2.0 millimeters per second in contact with a physiological fluid.

5. The method according to claim 2 wherein the fibrous wicking material consists of a fabric devoid of cotton.

6. The method of claim 1 wherein the glow discharge gas plasma comprises three-fifths oxygen.

7. A diagnostic test strip suitable for analysis of an analyte in a physiological fluid comprising an immobilized reagent means for detection and measurement of the analyte, a fibrous wicking material in the form of a sheet or cloth having a portion thereof in contact with the immobilized reagent means, and a holder for said reagent means and wicking material, wherein the wicking material has been surface-modified by exposure to a glow discharge gas plasma and exhibits a horizontal wicking rate of at least about 1.0 millimeter per second toward a physiological fluid, wherein also a portion of a sample of physiological fluid placed on said wicking material at a site apart from said reagent means is conveyed by wicking to said reagent means for analysis.

8. The diagnostic test strip according to claim 7 wherein the glow discharge gas plasma is formed in a gaseous blend composed predominantly of a mixture of oxygen with a saturated alkane chosen from the group consisting of methane, ethane and propane.

9. The diagnostic test strip according to claim 8 wherein the fibrous wicking material consists of a woven cotton-polyester fabric.

10. The diagnostic test strip according to claim 9 wherein the woven cotton-polyester fabric exhibits a horizontal wicking rate of at least about 2.0 millimeters per second toward a physiological fluid.

11. The diagnostic test strip according to claim 8 wherein the fibrous wicking material consists of a fabric devoid of cotton.

12. The diagnostic test strip according to claim 7 wherein the glow discharge gas plasma comprises three-fifths oxygen.

13. The diagnostic test strip according to claim 8 wherein said combination of oxygen and alkane produces a thin and tightly crosslinked veneer on the surface of the wicking material for maximum wicking.

14. A wick comprising a fibrous wicking material in the form of a sheet or cloth which has been surface-modified by exposure to a glow discharge gas plasma so as to exhibit a horizontal wicking rate of at least about 1.0 millimeter per second in contact with a physiological fluid.

15. The wick according to claim 14 wherein the glow discharge gas plasma is formed in a gaseous blend compose predominantly of a mixture of oxygen with a saturated alkane chosen from the group consisting of methane, ethane and propane.

16. The wick according to claim 15 wherein the fibrous wicking material consists of a woven cotton-polyester fabric.

17. The wick according to claim 16 wherein the fibrous wicking material exhibits a horizontal wicking rate of at least about 2.0 millimeters per second in contact with a physiological fluid.

18. The wick according to claim 15 wherein the fibrous wicking material consists of a fabric devoid of cotton.

19. The wick according to claim 14 wherein said glow discharge gas plasma comprises three-fifths oxygen.

20. The wick according to claim 15 wherein said combination of oxygen and alkane produces a thin and tightly crosslinked veneer on the surface of the wicking material for maximum wicking.

* * * * *